United States Patent
Parker et al.

(10) Patent No.: US 6,887,960 B2
(45) Date of Patent: May 3, 2005

(54) BIOADHESIVE COMPOSITION

(75) Inventors: Hsing-Yeh Parker, Woodinville, WA (US); Allan Sachs Hoffman, Seattle, WA (US)

(73) Assignee: Rohm and Haas Company, Philadelphia, PA (US)

(*) Notice: Subject to any disclaimer, the term of this patent is extended or adjusted under 35 U.S.C. 154(b) by 27 days.

(21) Appl. No.: 09/777,266

(22) Filed: Feb. 5, 2001

(65) Prior Publication Data

US 2002/0007028 A1 Jan. 17, 2002

Related U.S. Application Data

(60) Provisional application No. 60/181,522, filed on Feb. 10, 2000.

(51) Int. Cl.[7] ............................................. C08J 220/46
(52) U.S. Cl. ................. 526/317.1; 526/303.1; 526/307.1; 526/319; 526/320; 526/329.7; 526/325; 526/332; 526/909; 424/487; 424/78.08
(58) Field of Search .................. 526/303.1, 307.1, 526/325, 318.4, 320, 332, 347, 317.1, 319, 329.7, 909; 424/487, 78.08

(56) References Cited

U.S. PATENT DOCUMENTS

| | | | |
|---|---|---|---|
| 4,158,736 A | 6/1979 | Lewis et al. | |
| 4,948,580 A | 8/1990 | Browning | |
| 5,204,109 A | 4/1993 | Akemi et al. | |
| 5,298,258 A | 3/1994 | Akemi et al. | |
| 5,324,879 A | 6/1994 | Hawthorne | |
| 5,362,826 A | 11/1994 | Berge et al. | |
| 5,710,227 A | 1/1998 | Freeman et al. | |
| 5,770,627 A | 6/1998 | Inoue et al. | |
| 6,437,070 B1 * | 8/2002 | Parker et al. ............... 526/325 |

FOREIGN PATENT DOCUMENTS

EP 0435200 7/1991

OTHER PUBLICATIONS

Dunn, R. L. and Ottenbrite, R. M., "Polymeric Drugs and Drug Delivery Systems", ACS Symposium Series, 469, 11–23, 1990.

* cited by examiner

*Primary Examiner*—Tatyana Zalukaeva
(74) *Attorney, Agent, or Firm*—Carl P. Hemenway

(57) ABSTRACT

A bioadhesive composition is disclosed which includes copolymer particles containing as polymerized units, terminally unsaturated acid-containing oligomers and ethylenically unsaturated nonionic monomers. A method of preparing the bioadhesive composition and a method of using the bioadhesive composition are also disclosed.

10 Claims, No Drawings

BIOADHESIVE COMPOSITION

CROSS REFERENCE TO RELATED PATENT APPLICATIONS

This is a non-provisional application of prior pending U.S. provisional application Ser. No. 60/181,522 filed Feb. 10, 2000.

This invention relates to a bioadhesive composition. In particular, this invention relates to a bioadhesive composition which contains copolymer particles and is prepared from nonionic monomer and acid containing oligomer.

The efficacy of a drug is dependent upon many factors including the delivery of the drug or the drug precursor to the proper site within the body. Various delivery methods have been developed to transport drugs to target organs for subsequent release. The drug delivery methods often involve drug delivery materials or vehicles which provide for the controlled release of drugs, thus allowing increased residency times for the drugs without increasing their dosage. The controlled release of drugs permits low dosages to be used, thus minimizing potential drug side effects.

One drug delivery method known in the art is to incorporate a therapeutic substance into a polymer matrix. The polymer matrix functions as a pharmaceutical vehicle to carry the drug into the body, to protect the drug from deteriorating, and to provide controlled release of the drug. The polymer matrix does not have a therapeutic effect by itself. The therapeutic substance is physically blended with the polymer and is released from the polymer matrix by diffusion or by dissolution or degradation of the polymer matrix. Many polymers have been studied as polymer matrices for the delivery of drugs and are discussed in R. Dunn, *Polymer Matrices in Polymer Drugs and Drug Delivery Systems*, edited by R. L. Dunn and R. M. Ottenbrite, 1991.

A desirable property of a polymer matrix is the ability to adhere to biological surfaces such as mucosal surfaces to prolong drug delivery at a specific site in the body. The majority of polymers that may be used as bioadhesives for drug delivery adhere to epithelial tissue and to its mucus coating (such bioadhesives are hereinafter also referred to as "mucoadhesives"). The mucus coating is mucin, which is predominantly glycoproteins. Mucus-coated tissue is found in most nonparenteral routes of drug administration, including the eye, mouth, lungs, respiratory tract, gastrointestinal tract, nasal area, rectum, urinary tract and vagina.

High molecular weight linear poly(acrylic acid) (hereinafter referred to as "pAA") is a known mucoadhesive polymer and has been used in many drug formulations to prolong the retention time of the drug in the body. The loading of a hydrophobic drug may be enhanced and its release rate may be controlled and optimized by including hydrophobic components in the mucoadhesive polymer. U.S. Pat. No. 5,770,627 to Inoue et al. discloses an erodible bioadhesive based on a copolymer of acrylic acid with at least one hydrophobic component in the copolymer. These copolymers include block copolymers with hydrophobic and pAA blocks, and graft copolymers with either the hydrophobic block attached pendant to the pAA backbone or the pAA block attached pendant to a hydrophobic backbone. A preferable range for the ratio of hydrophobic component to pAA component was disclosed as 1 weight % to 50 weight %. The hydrophobic block and the pAA block are polymerized separately and additional synthesis is required to join the hydrophobic and pAA components through complementary reactive groups.

There is an on-going need for facile synthetic methods to prepare bioadhesive polymers. Applicants have discovered that copolymers prepared from a single step reaction of terminally unsaturated acid containing oligomers and nonionic monomers provide copolymers containing acid-functional oligomeric side chains. These copolymers may be formed into particles with acid-rich surfaces. The applicants have further discovered that the copolymer particles with acid-rich surfaces are useful as bioadhesives and for the controlled release of drugs.

The first aspect of this invention is directed to a bioadhesive composition which includes copolymer particles containing as polymerized units, from 60 weight % to 99 weight % based on weight of the copolymer particles, of at least one ethylenically unsaturated nonionic monomer and from 40 weight % to 1 weight % based on weight of the copolymer particles, of at least one oligomer selected from the group of oligomers with formulas:

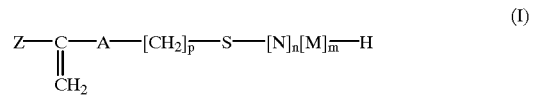

(I)

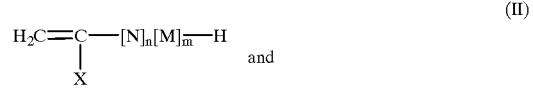

(II)

and

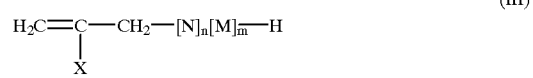

(III)

wherein N is the residue of an ethylenically unsaturated carboxylic acid monomer of the formula:

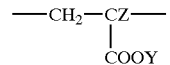

wherein M is the residue of a second ethylenically unsaturated monomer of the formula

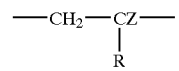

wherein the N and M residues are randomly arranged in the oligomer;

wherein m is the total number of M residues in the oligomer and is in the range of 0 to 150;

wherein n is the total number of N residues in the oligomer and is in the range of 2 to 300;

wherein n is greater than or equal to m;

wherein the sum of n and m is in the range of 2 to 300;

wherein A is a linker group selected from the group consisting of ester, urethane, amide, amine, and ether linkages;

wherein p is in the range of 1 to 20;

wherein X is selected from the group consisting of —COOY and R;

wherein R is selected from phenyl radicals, substituted phenyl radicals, —CONH$_2$, —CONHR', —CONR'R', —CN, —CCOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms;

wherein Y is independently selected from the group consisting of H, NH$_4$, alkali metals and alkaline earth metals; and wherein each Z is independently selected from the group consisting of H and CH$_3$.

In the second aspect of the present invention, there is provided a process for preparing a bioadhesive composition containing copolymer particles which includes the steps of providing a reaction mixture containing from 60 weight % to 99 weight %  based on weight of the copolymer particles, of at least one ethylenically unsaturated nonionic monomer and from 40 weight % to 1 weight % based on weight of the copolymer particles, of at least one oligomer selected from the group of oligomers with formulas:

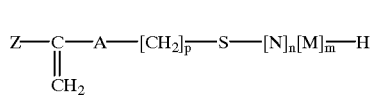

(I)

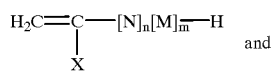 and (II)

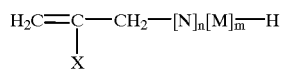

(III)

wherein N is the residue of an ethylenically unsaturated carboxylic acid monomer of the formula:

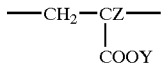

wherein M is the residue of a second ethylenically unsaturated monomer of the formula

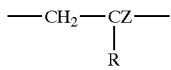

wherein the N and M residues are randomly arranged in the oligomer;

wherein m is the total number of M residues in the oligomer and is in the range of 0 to 150;

wherein n is the total number of N residues in the oligomer and is in the range of 2 to 300;

wherein n is greater than or equal to m;

wherein the sum of n and m is in the range of 2 to 300;

wherein A is a linker group selected from the group consisting of ester, urethane, amide, amine, and ether linkages;

wherein p is in the range of 1 to 20;

wherein X is selected from the group consisting of —COOY and R;

wherein R is selected from phenyl radicals, substituted phenyl radicals, —CONH$_2$, —CONHR', —CONR'R', —CN, —CCOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms;

wherein Y is independently selected from the group consisting of H, NH$_4$, alkali metals and alkaline earth metals; and wherein each Z is independently selected from the group consisting of H and CH$_3$; the step of polymerizing the reaction mixture; and the optional step of forming copolymer particles.

In the third aspect of this invention, there is provided a method of using a bioadhesive composition including preparing a composition containing copolymer particles and at least one therapeutic agent, wherein the copolymer particles include, as polymerized units, from 60 weight % to 99 weight % based on weight of the copolymer particles, of at least one ethylenically unsaturated nonionic monomer and from 40 weight % to 1 weight % based on weight of the copolymer particles, of at least one oligomer selected from the group of oligomers with formulas:

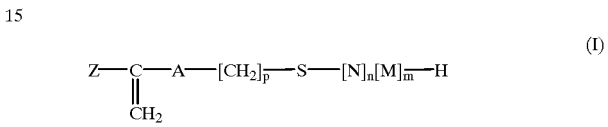

(I)

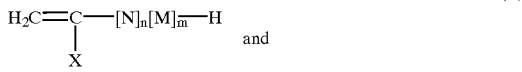 and (II)

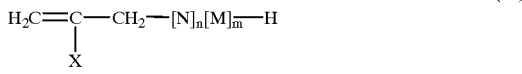

(III)

wherein N is the residue of an ethylenically unsaturated carboxylic acid monomer and has the formula:

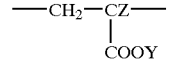

wherein M is the residue of a second ethylenically unsaturated monomer and has the formula:

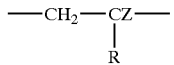

wherein the N and M residues are randomly arranged in the oligomer;

wherein m is the total number of M residues in the oligomer and is in the range of 0 to 150;

wherein n is the total number of N residues in the oligomer and is in the range of 2 to 300;

wherein n is greater than or equal to m;

wherein the sum of n and m is in the range of 2 to 300;

wherein A is a linker group selected from the group consisting of ester, urethane, amide, amine, and ether linkages;

wherein p is in the range of 1 to 20;

wherein X is selected from the group consisting of —COOY and R;

wherein R is selected from phenyl radicals, substituted phenyl radicals, —CONH$_2$, —CONHR', —CONR'R', —CN, —COOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms;

wherein Y is independently selected from the group consisting of H, NH$_4$, alkali metals and alkaline earth metals; and wherein each Z is independently selected from the group consisting of H and $CH_3$; optionally, isolating the bioadhesive composition; and administering the bioadhesive composition to body.

As used herein, the term "(meth)acrylate" denotes both "acrylate" and "methacrylate" and "(meth)acrylic" denotes both "methacrylic" and "acrylic."

The bioadhesive composition of the present invention includes copolymers which are prepared by the polymerization of oligomers, in particular, terminally unsaturated acid-containing oligomers, with nonionic monomers. The copolymer has a nonionic polymer backbone with pendant acid-containing sidechains covalently bonded to the backbone.

The terminally unsaturated acid-containing oligomers, referred to herein as "oligomer", have a single terminal unsaturation and include as polymerized units, monomers with acid groups. These oligomers are known in the art and are also referred to as macromonomers or macromers. The terminal unsaturation and the section of the oligomer with the acid groups, may be attached directly or through a linker group.

Suitable oligomers are:

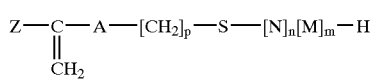  (I)

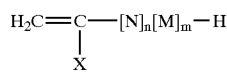  (II)

and

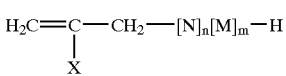  (III)

wherein N is the residue of an ethylenically unsaturated carboxylic acid monomer and has the formula:

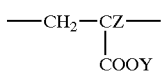

wherein M is the residue of a second ethylenically unsaturated monomer and has the formula

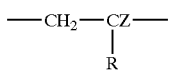

wherein the N and M residues are randomly arranged in the oligomer;

wherein m is the total number of M residues in the oligomer and is in the range of 0 to 150; wherein n is the total number of N residues in the oligomer and is in the range of 2 to 300; wherein n is greater than or equal to m; wherein the sum of n and m is in the range of 2 to 300; wherein A is a linker group selected from the group consisting of ester, urethane, amide, amine, and ether linkages; wherein p is in the range of 1 to 20;

wherein X is selected from the group consisting of —COOY and R; wherein R is selected from phenyl radicals, substituted phenyl radicals, —$CONH_2$, —CONHR', —CONR'R', —CN, —CCOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms; wherein Y is independently selected from the group consisting of H, $NH_4$, alkali metals and alkaline earth metals; and wherein each Z is independently selected from the group consisting of H and $CH_3$.

The oligomers may be polymerized from at least one ethylenically unsaturated carboxylic acid monomer and optionally at least one second ethylenically unsaturated monomer. Suitable ethylenically unsaturated carboxylic acid monomers include acrylic acid, methacrylic acid, beta-acryloxypropionic acid, ethacrylic acid, α-chloroacrylic acid, α-vinylacrylic acid, crotonic acid, α-phenylacrylic acid, cinnamic acid, chlorocinnamic acid, and β-styrylacrylic acid. Preferred ethylenically unsaturated carboxylic acid monomers are acrylic acid and methacrylic acid.

The second ethylenically unsaturated monomer includes styrene, vinyltoluene, (α-methylstyrene, vinylnaphthalene, vinyl acetate, vinyl versatate, vinyl chloride, (meth)acrylonitrile, (meth)acrylamide, mono- and di-substituted (meth)acrylamide, various ($C_1$–$C_{20}$)alkyl esters of (meth)acrylic acid; for example, methyl (meth)acrylate, ethyl (meth)acrylate, n-butyl (meth)acrylate, isobutyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, n-amyl (meth)acrylate, neopentyl (meth)acrylate, cyclopentyl (meth)acrylate, lauryl (meth)acrylate, oleyl (meth)acrylate, palmityl (meth)acrylate, and stearyl (meth)acrylate; and other (meth)acrylates such as isobornyl (meth)acrylate, benzyl (meth)acrylate, phenyl (meth)acrylate, 2-bromoethyl (meth)acrylate, 2-phenylethyl (meth)acrylate, and 1-naphthyl (meth)acrylate; alkoxyalkyl (meth)acrylate such as ethoxyethyl (meth)acrylate. The oligomers contain from 50 to 100 mole percent ethylenically unsaturated carboxylic acid monomer, preferably from 70 to 100 mole percent, and most preferably from 90 to 100 mole percent of these monomers.

The oligomers may be prepared by various conventional synthetic methods including anionic polymerization as disclosed in U.S. Pat. No. 4,158,736, radical polymerization with chain transfer agents such as cobalt complexes as described in U.S. Pat. No. 5,324,879, catalytic chain transfer polymerization with terminally unsaturated oligomers used as chain transfer agents as described in U.S. Pat. No. 5,362,826, and high temperature radical polymerization as described in U.S. Pat. No. 5,710,227. The terminally unsaturated oligomers of formula I may be prepared by conventional radical polymerization using a hydroxy-functional chain transfer agent such as 2-mercaptoethanol followed by the reaction of the hydroxyl group with an ethylenically unsaturated monomer with a complimentary reactive group to attach the terminal unsaturation. Examples of ethylenically unsaturated monomers with a complimentary reactive group include glycidyl (meth)acrylate, isocyanatoethyl (meth)acrylate, or (meth)acrylic acid. The ethylenically unsaturated monomers with a complimentary reactive group may be attached to the fragment of the hydroxy-functional chain transfer agent by various linkages including ether, urethane, amide, amine, or ester linkages. The oligomers of formulas I, II, and III may be prepared by bulk, solution, and emulsion polymerization using batch, semicontinuous, or continuous processes.

Another method to prepare the oligomers is polymerization of esters of ethylenically unsaturated carboxylic acid monomers such as ethyl acrylate, butyl acrylate, or methyl methacrylate followed by the partial or complete hydrolysis of the ester groups to obtain the carboxylic acid functionalities.

The copolymer includes as polymerized units from 60 to 99 weight % ethylenically unsaturated nonionic monomers. The ethylenically unsaturated nonionic monomers include monomers such as styrene, butadiene, α-methylstyrene, vinyltoluene, ethylene, vinylnaphthalene, vinyl acetate, vinyl versatate, vinyl chloride, vinylidene chloride, acrylonitrile, methacrylonitrile, (meth)acrylamide, mono- and di-substituted (meth)acrylamides, and various ($C_1$–$C_{20}$) alkyl esters of (meth)acrylic acid; for example, methyl (meth)acrylate, ethyl (meth)acrylate, n-butyl (meth)acrylate, isobutyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, n-amyl (meth)acrylate, neopentyl (meth)acrylate, cyclopentyl (meth)acrylate, lauryl (meth)acrylate, oleyl (meth)acrylate, palmityl (meth)acrylate, and stearyl (meth)acrylate; other (meth)acrylates such as isobornyl (meth)acrylate, benzyl (meth)acrylate, phenyl (meth)acrylate, 2-bromoethyl (meth)acrylate, 2-phenylethyl (meth)acrylate, and 1-naphthyl (meth)acrylate. Mixtures of these monomers may be used to prepare the copolymer. Some ethylenically unsaturated nonionic monomers may contain functionality, such as, but not limited to, hydroxy, amido, aldehyde, amino, ureido, and polyether. Examples include hydroxy-functional monomers such as 2-hydroxyethyl (meth)acrylate, hydroxypropyl (meth)acrylate, and polyethyleneglycol (meth)acrylate; aldehyde-functional monomers such as (meth)acrolein; amino-functional monomers such as dimethylaminoethyl (meth)acrylate; amido-functional monomers such as substituted (meth)acrylamides and diacetone acrylamide; epoxy-functional monomers such as glycidyl (meth)acrylate. Other ethylenically unsaturated nonionic monomers containing functionality include acetoacetoxy ethyl methacrylate, dicyclopentadienyl (meth)acrylate, dimethyl meta-isopropenyl benzyl isocyanate, isocyanato ethyl methacrylate, N-vinyl pyrrolidone, and N,N'-dimethylamino (meth)acrylate. In addition, this includes polymerizable surfactants, including for example but not limited to Trem LF-40 (Henkel Corporation). Further, another type of ethylenically unsaturated nonionic monomer with functionality includes multi-ethylenically unsaturated monomers which may be used to raise the molecular weight and crosslink the polymer. Examples of multi-ethylenically unsaturated monomers that can be used include allyl (meth)acrylate, tripropylene glycol di(meth)acrylate, diethylene glycol di(meth)acrylate, ethylene glycol di(meth)acrylate, 1,6-hexanediol di(meth)acrylate, 1,3-butylene glycol di(meth)acrylate, polyalkylene glycol di(meth)acrylate, diallyl phthalate, trimethylolpropane tri(meth)acrylate, divinylbenzene, divinyltoluene, trivinylbenzene, and divinylnaphthalene. The monomer mixture that is polymerized to form the copolymer may optionally contain from 0% to 10% by weight, based on the weight of the polymer particles, of ethylenically unsaturated nonionic monomers with functionality.

The copolymer of the present invention may also contain from 0 to 5 weight %, based on the weight of the copolymer, of ethylenically unsaturated carboxylic acid monomer, ethylenically unsaturated inorganic acid monomer, or combinations thereof. Ethylenically unsaturated carboxylic acid monomers include acrylic acid, methacrylic acid, crotonic acid, fumaric acid, maleic acid, mono-methyl itaconate, mono-methyl fumarate, monobutyl fumarate, and maleic anhydride. Ethylenically unsaturated inorganic acid monomers include phosphoethyl methacrylate, sodium vinyl sulfonate, and 2-acrylamido-2-methyl-1-propanesulfonic acid. Preferred ethylenically unsaturated carboxylic acid monomers include methacrylic acid and acrylic acid. The addition of monomers with acid functionality into the copolymer allows the modification of the hydrophobicity of the copolymer which may affect the uptake and release of the therapeutic agent.

Various polymerization processes are known in the art to prepare the copolymers of this invention. Suitable processes include bulk, solution, suspension, and emulsion polymerizations which can be continuous, semicontinuous, or batch processes. The solvent or mixtures of solvents for solution, suspension and emulsion polymerizations may include water and organic solvents including alcohols. The choice of solvents or mixtures of solvents is dependent upon many factors including the polymerization process, monomer solubility, and solubility of the copolymer. Various synthesis adjuvants may be used including initiators, chain transfer agents, surfactants, and buffers.

The copolymer of the present invention has weight average molecular weights in the range of 5,000 to greater than 5,000,000, preferably in the range of 10,000 to 2,000,000, and most preferably in the range of 20,000 to 1,000,000, as measured by gel permeation chromatography. The copolymer may contain from 1 to 40% by weight, preferably from 3 to 30% by weight, and most preferably from 5 to 20% by weight oligomer as polymerized units, based on the weight of copolymer.

The bioadhesive composition of the present invention includes copolymer particles which may be prepared from the copolymer by various methods. The copolymer particles may be formed in a polymerization process that also forms the copolymer as in emulsion and suspension polymerizations. Alternately, the copolymer particles may be formed by solubilizing the copolymer in a theta solvent and separating the copolymer into particles by the addition of a suitable solvent such as water. Copolymer particles may also be prepared by emulsification techniques known in the art. In aqueous medium, the copolymer may form a particle with a predominately hydrophobic core and a hydrophilic shell which is enriched in carboxylic acid. In one embodiment, the copolymer particle is a hydrophobic particle with a plurality of acid-functional side chains attached to the particle surface. The particle size of the copolymer particles may affect the drug delivery ability of the bioadhesive composition. For example, smaller copolymer particles are more easily absorbed or may more readily penetrate epithelial surfaces. Further, smaller copolymer particles may form more stable colloids. The preferred particle diameters for the copolymer particles are in the range of 0.01 μm to 100 μm, preferably in the range of 0.03 μm to 10 μm, and most preferably in the range of 0.05 μm to 1 μm.

While not wishing to be bound by theory, applicants believe that the copolymer of the invention is able to function as a mucoadhesive by the formation of an interpolymer complex, including hydrogen bonding and ionic interactions, between the acid functionality on the sidechains of the copolymer particle and the glycoprotein component of the mucin.

A therapeutic substance of interest may be combined with, absorbed or imbibed into, or otherwise associated with the copolymer particle prior to administration to the body. The therapeutic substance may be introduced to the reaction mixture during the polymerization of the copolymer or added to the copolymer or the copolymer solution after the polymerization reaction but prior to formation of copolymer particles. The bioadhesive composition which includes the copolymer particles and the therapeutic substance is then administered to the body by various methods known in the art including direct application, ingestion, injection, and inhalation. The bioadhesive composition then adheres to the mucous layer of the entry route and the drug is retained for some period of time greater than would be expected without the bioadhesive composition. The therapeutic substance of interest is thus delivered to the body in a more efficient and localized manner.

The bioadhesive compositions including the copolymer particles of this invention are suitable for the delivery and sustained release of many therapeutic substances including pharmaceutical, cosmetic, or prophylactic substances such as drug compounds, drug precursors, peptides, proteins, perfumes, and fragrances, or mixtures thereof. The bioadhesive composition may also be used for the delivery of pesticides, fungicides, mildewcides, and biocides.

The bioadhesive composition including the therapeutic substance may be administered by topical routes of administration to mucosal tissue such as the eye, mouth, gastrointestinal tract, respiratory tract, nasal area, rectum, urinary tract, and vagina. Topical administration also includes application to the skin, scalp, an open wound, and a burn. Other methods of application include systemic administration such as oral administration and injection.

In the following Examples, the following abbreviations were used:

| | |
|---|---|
| MMA | methyl methacrylate |
| BA | n-butyl acrylate |
| AA | acrylic acid |
| o-AA | terminally unsaturated acrylic acid oligomer of Formula II |

-continued

| | |
|---|---|
| with | m = 0 |
| THF | tetrahydrofuran |
| DMF | N,N-dimethylformamide |
| V-60 | Vazo V-60 initiator (Waco Chemical Co.) - 2,2'-Azo-bisisobutyronitrile |
| PGM | porcine gastric mucin (Sigma Chemical) |
| meq | milliequivalent |

EXAMPLE 1

Preparation of poly(acrylic acid-g-methyl methacrylate/n-butyl acrylate) [P(MMA BA/o-AA)] Using Acrylic Acid Oligomers.

Synthesis: In a 1-liter round bottom flask which was equipped with a mechanical stirrer, a condenser, and a thermocouple, 26 g of acrylic acid macromer (o-AA) solid was dissolved in 200 ml of isopropanol and 25 ml of water. For the o-AA provided as a 50% aqueous solution, 52 g of the o-AA solution was mixed with 200 ml isopropanol. The solution was agitated at 200 rpm and heated to 70° C. A nitrogen atmosphere was maintained within the reactor for the polymerization reaction. A monomer mixture was prepared containing 52.25 g MMA, 22.5 g BA, 1.6 g Vazo V-60 (Waco Chemical Co.), and 30 ml isopropanol. An initial charge of 50 ml of the monomer mixture was added at a pump rate of 14 ml/min. After a 2° C. temperature rise, the remaining monomer mixture was added to the reactor at 0.3 ml/min. over a period of 3 hours. The reaction mixture was cooled to 60° C. and agitated under a nitrogen atmosphere overnight. Analysis of Polymer: The resulting copolymer was analyzed for grafted acrylic acid by separating the copolymer from unreacted o-AA and other acrylic acid oligomers. First, 1 ml of the final reaction mixture containing the copolymer was added to 5 ml water with vigorous shaking to precipitate the copolymer. The resulting suspension was centrifuged at 10,000 rpm for 30 min. The supernatant was decanted and the steps of suspending the copolymer solids in water, centrifuging, and decanting were repeated. After three washes, the copolymer solids were dried in vacuum at room temperature, dissolved in THF, and titrated for grafted carboxylic acid. The supernatant solutions from the repeated centrifuge/decanting steps were titrated individually and the results were combined as the total unreacted o-AA. The separated copolymer was also analyzed for molecular weight by gel permeation chromatography (GPC). The glass transition temperature of the polymer was determined by differential scanning calorimetry (DSC).

TABLE 1.1

Composition and Properties of MMA/BA/o-AA Copolymers

| | Composition- Wt% MMA/BA/o-AA | Mw of o-AA | Mw/Mn of Copolymer | Tg (° C.) |
|---|---|---|---|---|
| Example 1-1 | 58.6/25.1/16.3 | 1,200 | 28,600/6,900 | 54 |
| Example 1-2 | 60.0/25.7/14.3 | 2,300 | 30,800/8,300 | 58 |
| Example 1-3 | 59.5/25.5/15.1 | 4,500 | 25,000/6,500 | 52 |
| Example 1-4 | 63.4/27.2/9.4 | 19,000 | 29,000/7,300 | 46 |

Purification of Copolymer: The general procedure for purifying the copolymer was to precipitate the copolymer from the final reaction mixture by adding 3 parts water for each part reaction mixture with agitation, on a volume basis. The copolymer solid was washed with deionized water until the pH of the filtrate was 5.0 or higher. As the form of the precipitate varied with the molecular weight of the grafted o-AA, various methods were used to collect the precipitated polymer. Example 1-1 formed a course precipitate and was collected by filtration. The precipitate of example 1-2 formed fine particles and was collected by centrifugation followed by washing with water. Examples 1-3 and 1-4 formed stable emulsions and were purified by ultrafiltration with a 0.06 µm membrane (Spectrum MiniKros Tangential Flow Ultrafiltration module from Spectrum Laboratories, Inc, Laguna Hills, Calif.). The purified copolymer was dried by freeze drying.

Preparation of Copolymer Particles: The dried copolymer was dissolved at approximately 6 weight % solution in isopropanol/DMF with the DMF minimized to less than 20 volume %. The solution was filtered through a 100 μm sieve and further diluted with the same solvent mixture to a 1–3 weight % concentration. Next, 3–4 volumes of deionized water was added to the copolymer solution with vigorous stirring to form the copolymer particles and was mixed for 10 minutes. The addition rate of water to the polymer solution affected the particle size. Gradual addition of water produced larger diameter particles and rapid addition of water produced smaller diameter particles. The organic solvent was removed by evaporation. The copolymer latex was concentrated by ultrafiltration using a 400 ml stirred cell fitted with a 500,000 molecular weight cutoff polyvinylidene fluoride (PVDF) membrane. After the total volume was reduced to 40 ml, the particles were washed with four 350ml water rinses. The particle size was determined by light scattering with a Brookhaven BI-9000 AT photon correlator with BI-200 SM goniometer. Acid Content of Copolymer Particle: The acid content of the copolymer particles was determined by titrating the purified copolymer with base. Titration of the copolymer particles in water and the solubilized copolymer in THF gave similar results indicating that the acid was located at or near the surface of the copolymer particle.

TABLE 1.2.

Copolymer Particles Prepared from MMA/BA/o-AA Copolymers

|  | Copolymer of: | Solids wt % | Particle Diameter (nm) |
|---|---|---|---|
| Example 2.1 | Example 1–1 | 4.59 | 89 |
| Example 2.2 | Example 1–2 | 4.45 | 87 |
| Example 2.3 | Example 1–3 | 9.31 | 130 |
| Example 2.4 | Example 1–4 | 4.87 | 118 |
| Example 2.5 | Example 1–4 | 1.46 | 239 |

EXAMPLE 2
Complexation of the MMA/BA/o-AA Lattices

The mucoadhesion of the copolymers particle of Example 2 (2.1-2.5) to the mucus layer of epithelial tissue was established by measuring their complexation with porcine gastric mucin (PGM). The complexation of the lattices with the PGM was determined by a potentiometric titration. The basis for this method was complexation of pAA with another polymer decreases the dissociation of the carboxylic acid groups on the pAA with a concomitant increase in the pH. This can be represented by:

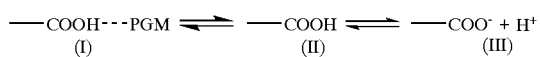

where (I) represents carboxylic acid groups on the pAA complexed with PGM, (II,) represents undissociated carboxylic acid on the pAA, and (III) represents dissociated carboxylic acid groups. The degree of complexation, θ, was calculated by:

$$\theta = 1 - \frac{[H^+]^2}{[H^+]_0^2} = 1 - \left(\frac{10^{-pH}}{10^{-pH_0}}\right)^2$$

where [H$^+$] was the H$^+$ concentration in the presence of the PGM and [H$^+$]$_o$ was the H$^+$ concentration without PGM. A value of θ equal to 1 denotes complete complexation of the carboxylic acid groups.

The MMA/BA/o-AA latex solutions in Table 2.1 were titrated with standardized KOH to determine their carboxylic acid concentrations. The copolymer latices were diluted to carboxylic acid concentrations of 0.002 M and 0.005 M using deionized water.

The PGM was dissolved in water and dialyzed against deionized water at 4° C. for two weeks until the conductivity of the water reservoir reads <5 μmoh and the pH was >6. The dialyzed PGM solution was freeze dried and redissolved in deionized water to form a 5 wt % solution.

The complexation constants were determined by adding aliquots of the PGM solution to the MMA/BA/o-AA latex solutions and recording the pH.

TABLE 2.1

Complexation of PGM with MMA/BA/o-AA Latices at a Carboxylic Acid Concentration of 0.002M

| PGM | θ | | | | |
|---|---|---|---|---|---|
| (g/meq COOH) | Example 2.1 | Example 2.2 | Example 2.3 | Example 2.4 | Example 2.5 |
| 0.00 | 0.0000 | 0.0000 | 0.0000 | 0.0000 | 0.0000 |
| 0.02 | 0.5344 | 0.7822 | 0.6881 | 0.6643 | 0.7382 |
| 0.04 | 0.7488 | 0.9198 | 0.8486 | 0.8325 | 0.9125 |
| 0.06 | 0.8437 | 0.9591 | 0.9161 | 0.9067 | 0.9501 |
| 0.08 | 0.8909 | 0.9742 | 0.9393 | 0.9348 | 0.9664 |
| 0.10 | 0.9241 | 0.9849 | 0.9526 | 0.9519 | 0.9745 |
| 0.12 | 0.9414 | 0.9897 | 0.9666 | 0.9653 | 0.9829 |
| 0.14 | 0.9591 | 0.9923 | 0.9736 | 0.9713 | 0.9880 |
| 0.16 | 0.9672 | 0.9942 | 0.9807 | 0.9773 | 0.9905 |
| 0.18 | 0.9738 | 0.9955 | 0.9856 | 0.9825 | 0.9926 |
| 0.20 | 0.9783 | 0.9960 | 0.9879 | 0.9860 | 0.9942 |

TABLE 2.2

Complexation of PGM with MMA/BA/o-AA Latices at a Carboxylic Acid Concentration of 0.005M

| PGM | θ | | | | |
|---|---|---|---|---|---|
| (g/meq COOH) | Example 2.1 | Example 2.2 | Example 2.3 | Example 2.4 | Example 2.5 |
| 0.00 | 0.0000 | 0.0000 | 0.0000 | 0.0000 | 0.0000 |
| 0.04 | 0.9403 | 0.9324 | 0.9435 | 0.9315 | 0.9018 |
| 0.08 | 0.9667 | 0.9785 | 0.9786 | 0.9698 | 0.9755 |
| 0.12 | 0.9838 | 0.9893 | 0.9921 | 0.9804 | 0.9895 |
| 0.16 | 0.9905 | 0.9935 | 0.9934 | 0.9876 | 0.9941 |
| 0.20 | 0.9919 | 0.9957 | 0.9952 | 0.9920 | 0.9965 |
| 0.24 | 0.9952 | 0.9970 | 0.9972 | 0.9942 | 0.9976 |
| 0.28 | 0.9970 | 0.9979 | 0.9980 | 0.9964 | 0.9985 |
| 0.32 | 0.9977 | 0.9982 | 0.9981 | 0.9973 | 0.9989 |
| 0.36 | 0.9983 | 0.9988 | 0.9985 | 0.9982 | 0.9991 |
| 0.40 | 0.9988 | 0.9991 | 0.9999 | 0.9985 | 0.9994 |

TABLE 2.3

Complexation of PGM with MMA/BA/o-AA Latices at a Carboxylic Acid Concentration of 0.002M in 0.1M Sodium Chloride

| PGM | θ | | | | |
|---|---|---|---|---|---|
| (g/meq COOH) | Example 2.1 | Example 2.2 | Example 2.3 | Example 2.4 | Example 2.5 |
| 0.00 | 0.0000 | 0.0000 | 0.0000 | 0.0000 | 0.0000 |
| 0.02 | 0.6643 | 0.6564 | 0.6037 | 0.5812 | 0.6268 |
| 0.04 | 0.8564 | 0.8528 | 0.8059 | 0.7958 | 0.8348 |
| 0.06 | 0.9357 | 0.9308 | 0.9080 | 0.8995 | 0.9164 |
| 0.08 | 0.9697 | 0.9670 | 0.9487 | 0.9458 | 0.9545 |
| 0.1 | 0.9822 | 0.9809 | 0.9694 | 0.9685 | 0.9736 |
| 0.12 | 0.9887 | 0.9882 | 0.9808 | 0.9799 | 0.9828 |
| 0.14 | 0.9921 | 0.9924 | 0.9866 | 0.9865 | 0.9878 |

TABLE 2.3-continued

Complexation of PGM with MMA/BA/o-AA Latices at a
Carboxylic Acid Concentration of 0.002M in 0.1M Sodium Chloride

| PGM (g/meq COOH) | θ | | | | |
|---|---|---|---|---|---|
| | Example 2.1 | Example 2.2 | Example 2.3 | Example 2.4 | Example 2.5 |
| 0.16 | 0.9948 | 0.9950 | 0.9910 | 0.9903 | 0.9907 |
| 0.18 | 0.9962 | 0.9965 | 0.9935 | 0.9929 | 0.9930 |
| 0.20 | 0.9971 | 0.9977 | 0.9950 | 0.9946 | 0.9947 |

TABLE 2.4

Complexation of PGM with MMA/BA/o-AA Latices at a
Carboxylic Acid Concentration of 0.005M in 0.1M Sodium Chloride

| PGM (g/meq COOH) | θ | | | | |
|---|---|---|---|---|---|
| | Example 2.1 | Example 2.2 | Example 2.3 | Example 2.4 | Example 2.5 |
| 0.00 | 0.0000 | 0.0000 | 0.0000 | 0.0000 | 0.0000 |
| 0.04 | 0.9195 | 0.7842 | 0.8310 | 0.8005 | 0.7772 |
| 0.08 | 0.9821 | 0.9381 | 0.9419 | 0.9336 | 0.9305 |
| 0.12 | 0.9948 | 0.9796 | 0.9772 | 0.9819 | 0.9774 |
| 0.16 | 0.9981 | 0.9911 | 0.9896 | 0.9926 | 0.9918 |
| 0.20 | 0.9992 | 0.9955 | 0.9948 | 0.9965 | 0.9960 |
| 0.24 | 0.9996 | 0.9976 | 0.9978 | 0.9978 | 0.9979 |
| 0.28 | 0.9998 | 0.9986 | 0.9988 | 0.9988 | 0.9989 |
| 0.32 | 0.9999 | 0.9991 | 0.9993 | 0.9992 | 0.9993 |
| 0.36 | 0.9999 | 0.9994 | 0.9995 | 0.9994 | 0.9996 |
| 0.40 | 0.9999 | — | 0.9997 | 0.9996 | 0.9997 |

A value of θ>0.5 is taken as demonstration of an effective level of mucoadhesion. The addition of PGM to the MMA/BA/o-AA latices gave complexation of the PGM with the carboxylic acid, indicating the MMA/BA/o-AA latices have the ability to adhere to the mucus layer of epithelial tissue and act as bioadhesives.

What is claimed is:

1. A process for preparing a bioadhesive composition comprising copolymer particles comprising:
   a) providing a reaction mixture comprising:
      i) from 60 weight % to 99 weight % based on weight of said copolymer particles, of at least one ethylenically unsaturated nonionic monomer and
      ii) from 40 weight % to 1 weight % based on weight of said copolymer particles, of at least one oligomer selected from the group of oligomers with formulas:

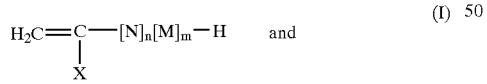 (I)

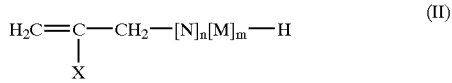 (II)

wherein N is the residue of an ethylenically unsaturated carboxylic acid monomer and has the formula:

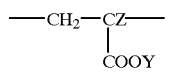

wherein M is the residue of a second ethylenically unsaturated monomer and has the formula:

—CH$_2$—CZ—
          |
          R wherein said N and M residues are randomly arranged in said oligomer; wherein m is the total number of M residues in said oligomer and is in t the range of 0 to 150;
   wherein n is the total number of N residues in said oligomer and is in the range of 2 to 300;
   wherein n is greater than or equal to m;
   wherein the sum of n and m is in the range of 2 to 300;
   wherein X is selected from the group consisting of —COOY and R;
   wherein R is selected from phenyl radicals, substituted phenyl radicals, —CONH$_2$, —CONHR', —CONR'R', —CN, —COOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms;
   wherein Y is independently selected from the group consisting of H, NH$_4$, alkali metals and alkaline earth metals; and
   wherein each Z is independently selected from the group consisting of H and CH$_3$,
   b) polymerizing said reaction mixture; and
   c) forming copolymer particles and d) adding a therapeutic substance.

2. The process of claim 1 wherein m=0 and X=—COOY.

3. The method of using a bioadhesive composition comprising:
   a) preparing a composition comprising copolymer particles and at least one therapeutic agent, wherein said copolymer particles comprise, as polymerized units, from 60 weight % to 99 weight % based on weight of said copolymer particles, of at least one ethylenically unsaturated nonionic monomer and from 40 weight % to 1 weight % based on weight of said copolymer particles, of at least one oligomer selected from the group of oligomers with formulas:

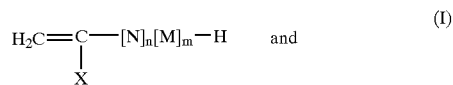 (I)

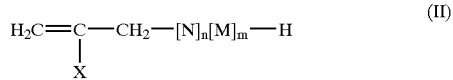 (II)

wherein N is the residue of an ethylenically unsaturated carboxylic acid monomer and has the formula:

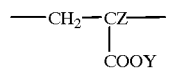

wherein M is the residue of a second ethylenically unsaturated monomer and has the formula:

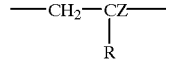

wherein said N and M residues are randomly arranged in said oligomer;

wherein m is the total number of M residues in said oligomer and is in t the range of 0 to 150;

wherein n is the total number of N residues in said oligomer and is in the range of 2 to 300;

wherein n is greater than or equal to m;

wherein the sum of n and m is in the range of 2 to 300.

4. The method of claim 3 wherein m=0 and X=—COOY.

5. The method of claim 3 wherein said copolymer particle comprises, as polymerized units, said oligomer in the range of 3 weight % to 30 weight %, based on weight of said copolymer particle.

6. A bioadhesive composition comprising copolymer particles comprising, as polymerized units, a) from 60 weight % to 99 weight % based on weight of said copolymer particles, of at least one ethylenically unsaturated nonionic monomer and b) from 40 weight % to 1 weight % based on weight of said copolymer particles, of at least one oligomer selected from the group of oligomers with formulas:

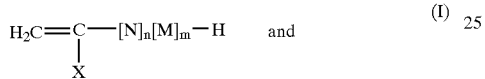 (I)

and

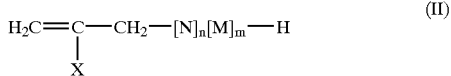 (II)

wherein N is the residue of an ethylenically unsaturated carboxylic acid monomer and has the formula:

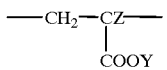

wherein M is the residue of a second ethylenically unsaturated monomer and has the formula:

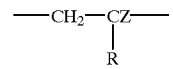

wherein said N and M residues are randomly arranged in said oligomer;

wherein m is the total number of M residues in said oligomer and is in the range of 0 to 150;

wherein n is the total number of N residues in said oligomer and is in the range of 2 to 300;

wherein n is greater than or equal to m;

wherein the sum of n and m is in the range of 2 to 300;

wherein X is selected from the group consisting of —COOY and R;

wherein R is selected from phenyl radicals, substituted phenyl radicals, —CONH$_2$, —CONHR', —CONR'R', —CN, —COOR', —OCOR', —Cl, and mixtures thereof, wherein R' is an alkyl or alkoxyalkyl radical independently selected from the group consisting of branched, unbranched, or cyclic hydrocarbon radicals having 1 to 18 carbon atoms;

wherein Y is independently selected from the group consisting of H, NH$_4$, alkali metals and alkaline earth metals; and wherein each Z is independently selected from the group consisting of H and CH$_3$, and a therapeutic substance.

7. The bioadhesive composition of claim 11 wherein m=0 and X=—COOY.

8. The bioadhesive composition of claim 6 wherein said copolymer particle comprises, as polymerized units, said oligomer in the range of 3 weight % to 30 weight %, based on weight of said copolymer particle.

9. The bioadhesive composition of claim 6 wherein said ethylenically unsaturated carboxylic acid monomer is selected from acrylic acid or methacrylic acid.

10. The bioadhesive composition of claim 6 wherein said copolymer particles have a diameter in the range of from 0.1 micron to 100 micron.

* * * * *